US011865284B2

United States Patent
Hoshino et al.

(10) Patent No.: US 11,865,284 B2
(45) Date of Patent: Jan. 9, 2024

(54) FLOW SENSOR FOR CEREBRAL FLUIDIC DEVICE

(71) Applicants: UNIVERSITY OF CONNECTICUT, Farmington, CT (US); YALE UNIVERSITY, New Haven, CT (US)

(72) Inventors: Kazunori Hoshino, Farmington, CT (US); Davina Jaiswal, Farmington, CT (US); Mengdi Bao, Farmington, CT (US); Garrett Soler, Farmington, CT (US); Ariane Garrett, Farmington, CT (US); Ryan Grant, Farmington, CT (US); Michael Diluna, Farmington, CT (US); Hitten Zaveri, Farmington, CT (US)

(73) Assignees: University of Connecticut, Farmington, CT (US); Yale University, New Haven, CT (US)

( * ) Notice: Subject to any disclaimer, the term of this patent is extended or adjusted under 35 U.S.C. 154(b) by 288 days.

(21) Appl. No.: 16/498,597

(22) PCT Filed: Mar. 29, 2018

(86) PCT No.: PCT/US2018/025238
§ 371 (c)(1),
(2) Date: Sep. 27, 2019

(87) PCT Pub. No.: WO2018/183737
PCT Pub. Date: Oct. 4, 2018

(65) Prior Publication Data
US 2020/0046951 A1 Feb. 13, 2020

Related U.S. Application Data

(60) Provisional application No. 62/478,707, filed on Mar. 30, 2017.

(51) Int. Cl.
*A61M 27/00* (2006.01)
*B33Y 80/00* (2015.01)

(52) U.S. Cl.
CPC .......... *A61M 27/006* (2013.01); *B33Y 80/00* (2014.12); *A61M 2205/0216* (2013.01);
(Continued)

(58) Field of Classification Search
CPC ........ A61M 27/006; A61M 2205/0216; A61M 2205/0294; A61M 2205/3306;
(Continued)

(56) References Cited

U.S. PATENT DOCUMENTS 5,520,632 A * 5/1996 Leveen ............... A61M 27/006
604/8
6,216,022 B1 * 4/2001 Tyrrell ............... A61B 5/14532
600/316
(Continued)

FOREIGN PATENT DOCUMENTS

WO WO-2015200712 A1 * 12/2015 .......... A61M 5/3286

OTHER PUBLICATIONS

Extended European Search Report for corresponding European application No. 18777778.4, dated Dec. 1, 2020.
(Continued)

*Primary Examiner* — Adam Marcetich
*Assistant Examiner* — Rachel O'Connell
(74) *Attorney, Agent, or Firm* — McDonnell Boehnen Hulbert & Berghoff LLP

(57) ABSTRACT

The present disclosure provides a fluidic device including (a) a first channel including a first inlet and a first outlet, (b) a second channel including a second inlet and a second outlet, wherein the second inlet of the second channel is in fluid communication with the first outlet of the first channel, and (c) a sensor positioned between the first outlet and the
(Continued)

second inlet, wherein the sensor includes a sensor configured to deflect in response to a flow between the first channel and the second channel.

21 Claims, 2 Drawing Sheets

(52) U.S. Cl.
CPC ............... *A61M 2205/0294* (2013.01); *A61M 2205/3306* (2013.01); *A61M 2205/3313* (2013.01); *A61M 2205/3334* (2013.01); *A61M 2205/702* (2013.01); *A61M 2207/00* (2013.01); *A61M 2210/0693* (2013.01)

(58) Field of Classification Search
CPC .. A61M 2205/3313; A61M 2205/3334; A61M 2205/702; A61M 2207/00; A61M 2210/0693; B33Y 80/00
See application file for complete search history.

(56) References Cited

U.S. PATENT DOCUMENTS

| | | | | |
|---|---|---|---|---|
| 8,694,079 | B1* | 4/2014 | LaFarge | A61B 5/4381 600/478 |
| 8,778,446 | B2 | 7/2014 | Mutharasan et al. | |
| 9,364,647 | B1* | 6/2016 | Beckman | A61M 27/006 |
| 2004/0082900 | A1* | 4/2004 | Luttich | A61M 27/006 604/9 |
| 2005/0072421 | A1* | 4/2005 | Suman | A61M 15/00 128/200.23 |
| 2008/0034840 | A1* | 2/2008 | Mutharasan | G01N 29/022 73/24.01 |
| 2009/0296223 | A1* | 12/2009 | Werner | G02B 3/0087 359/641 |
| 2010/0228179 | A1* | 9/2010 | Thomas | A61M 27/006 604/9 |
| 2011/0004158 | A1* | 1/2011 | Luciano | A61M 27/002 604/131 |
| 2011/0224595 | A1 | 9/2011 | Pedersen et al. | |
| 2011/0275912 | A1* | 11/2011 | Boyden | A61L 2/08 600/309 |
| 2011/0301575 | A1* | 12/2011 | Miesel | G01L 9/0072 604/891.1 |
| 2012/0095383 | A1* | 4/2012 | Radojicic | A61L 31/005 604/8 |
| 2012/0232461 | A1* | 9/2012 | Seaver | A61M 27/006 604/9 |
| 2012/0238835 | A1* | 9/2012 | Hyde | A61B 5/1459 600/302 |
| 2013/0220729 | A1* | 8/2013 | Daraio | G10K 15/00 181/175 |
| 2015/0133889 | A1* | 5/2015 | Campagnolo | A61M 5/16854 604/505 |
| 2015/0216684 | A1* | 8/2015 | Enzmann | A61F 2/848 623/1.36 |
| 2015/0224699 | A1* | 8/2015 | Larsen | B29C 48/155 264/176.1 |
| 2015/0297093 | A1 | 10/2015 | Goldie et al. | |
| 2017/0021145 | A1 | 1/2017 | Saul et al. | |

OTHER PUBLICATIONS

The International Search Report (ISR) with Written Opinion for PCT/US2018/025238 dated Jun. 26, 2018, pp. 1-8.
H2flow Controls Inc.: "FlowVis(r) Flow Meter Instruction Manual", Aug. 26, 2013, waterco.us/waterco/manuals/pool-spa/valves/flowvis-manual-2-8-pages-lo-res-6-12-2013-f-.pdf.

* cited by examiner

FLOW SENSOR FOR CEREBRAL FLUIDIC DEVICE

CROSS-REFERENCE TO RELATED APPLICATION

This application is a U.S. national phase of International Application No. PCT/US2018/025238, filed on Mar. 29, 2018, which claims priority to U.S. Provisional Application No. 62/478,707, filed Mar. 30, 2017, both of which are incorporated by reference herein in their entirety.

BACKGROUND

Cerebrospinal fluid (CSF) is a body fluid contained in the brain ventricles and the cranial and spinal subarachnoid spaces. It is renewed about four times every 24 hours. Arterial pulse waves largely decide CSF flow dynamics and pressure from sites of secretion to sites of absorption. Additionally, CSF circulation is effected by the subject's posture, respiratory waves, jugular venous pressure and physical effort. Recent research shows that CSF plays an essential role in regulating neuronal function and maintaining homeostasis of the interstitial fluid in the brain.

Hydrocephalus is a neurological condition classified by the abnormal accumulation of CSF in the brain. Hydrocephalus is a prevalent condition, affecting 4-6 per 1000 people, which almost always requires treatment by a neurosurgeon in the developed world. It results from the accumulation of cerebrospinal fluid (CSF) within the intracranial ventricular system of the brain causing increased intracranial pressure (ICP) and significant neurological ailments. It can be secondary to CSF obstruction, inadequate absorption, or CSF overproduction. Hydrocephalus is progressive and can result in neurological deterioration or death.

Current treatments for hydrocephalus include installing a device to drain excess CSF. However, 40% of these devices fail within the first two years, and 98% fail within 10 years, which can lead to emergency room visits. However, there is no direct non-invasive way to assess whether the device is working properly. This can result in unnecessary procedures and consultations when the device is still working properly. Given the significant amount of implanted devices to treat CSF related conditions, clinicians and patients need a non-invasive and direct way to know if a device is functioning appropriately.

SUMMARY

A first example embodiment may include a fluidic device that includes a first channel that has a first inlet and a first outlet. The fluidic device also includes a second channel that has a second inlet and a second outlet. The second inlet of the second channel is in fluid communication with the first outlet of the first channel. The fluidic device also includes a sensor positioned between the first outlet and the second inlet. The sensor is configured to deflect in response to a flow between the first channel and the second channel.

A second example embodiment may include a method including positioning the fluidic device in a cerebral ventricle of a subject. The method may also include detecting, via a deflection in the sensor, a flow rate of a liquid between the first channel and the second channel.

A third example embodiment may include a non-transitory computer readable medium having stored thereon instructions, that when executed by one or more processors, cause an additive manufacturing machine to create one or more components of the fluidic device according to the first example embodiment.

A fourth example embodiment may include a non-transitory computer readable medium having stored thereon instructions, that when executed by one or more processors, cause a fluidic device to perform operations in accordance with the second example embodiment.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

Features, aspects, and advantages of the presently disclosed technology may be better understood with regard to the following description, appended claims, and accompanying drawings where:

Figure 1:
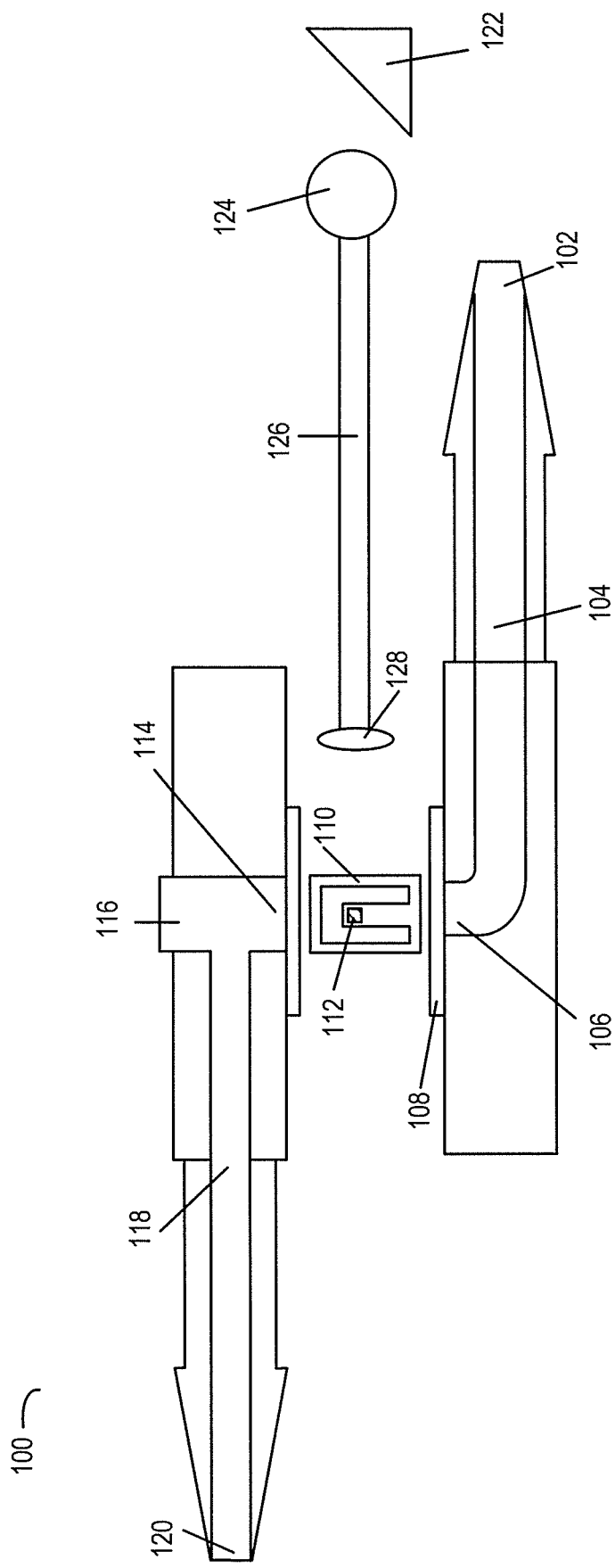
FIG. 1 shows an example fluidic device configuration, according to an example embodiment.

The drawings are for the purpose of illustrating example embodiments, but it is understood that the inventions are not limited to the arrangements and instrumentalities shown in the drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the Figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means +/−5%.

The concept behind fluidic devices and methods of using the fluidic devices as described herein is to provide a feedback system in which measured conditions and data provide parameters with which to examine fluidic device efficiency, any hardware malfunction or damage, and to significantly improve fluidic device functionality in order to meet the needs of the individualized subject. This precision medicine approach to, for example, hydrocephalus could be a key facet in treatment catering to the appropriate levels of CSF buildup for a specific subject. The fluidic devices and methods of using the fluidic devices described herein may also be used to treat conditions known to cause hydrocephalus or that are related to hydrocephalus. These conditions may include tumors, spina bifida, congenital aqueductal stenosis, craniosynostosis, dandy walker syndrome, arachnoid cyst, idiopathic intracranial hypertension. Additionally, the fluidic devices and methods of using the fluidic devices described herein could be used for any implantable fluidic devices including pain pumps, baclofen pumps, or could be also used to detect blood flow rate if connected to a blood vessel.

The fluidic device as described herein is used to detect proper CSF flow by testing the compartmental flow rate. The fluidic device may include a two-piece compartment and a sensor which is situated inside the compartment. Using a light source (e.g., laser or high-powered LED) focused on the sensor through an opening in the compartment, the internal flow rate may be measured by varying fluid flow rate and recording angle deviation. The reflected light, used to record angle variations, is captured by an imaging device (e.g., a camera) positioned above a subject's skin. In this way, the imaging device enables monitoring of the fluidic device without the need to broach the sealed compartment.

As a subject's skin becomes thicker, it may become difficult to focus light on the sensor due to diffusion of the light. To combat this diffusion, an optical system may be added to the fluidic device to spatially confine the light. This may result in adequate light being focused on the sensor. Any suitable optical system to spatially confine the light onto the sensor may be used.

In some embodiments, the optical system of the fluidic device may include a prism mirror that is configured to redirect light from the light source into the sensor by reflecting the light at a 90-degree angle. The prism mirror may redirect the light into a ball lens. The ball lens may focus the light into an optical fiber to reduce light loss. The optical fiber carries the light to a focusing lens. The focusing lens focuses light into a small location on the sensor, which reflects the light back through a subject's skin to be sensed by the imaging device.

In other embodiments, the optical system of the fluidic device may include the prism mirror and focusing lens as described above, but may alternatively include an aperture and a hollow metal tube. The aperture may receive the light from the prism mirror and focus the light into the hollow metal tube. The hollow metal tube may then carry the light to the focus lens. Other elements for spatial confinement of the light onto the sensor may be used.

FIG. 1 includes a fluidic device 100 used to detect proper flow of CSF. The fluidic device 100 includes a first inlet 102, a first channel 104, a first outlet 106, a layer 108, and a flow sensor 110 with a reflector 112. Fluidic device 100 also includes a second inlet 114, and opening 116, a second channel 118, and a second outlet 120. Fluidic device 100 may also include an optional optical system including prism mirror 122, a ball lens 124, an optical fiber 126, and a focusing lens 128. Prism mirror 122 may have a dimension of about 3 mm by 3 mm. Ball lens 124 may have a diameter of about 1 mm. Optical fiber 126 may have a diameter of about 0.5 mm. Focusing lens 128 may have a diameter of about 3 mm.

The optical system may be held and aligned to the sensor by an optical system holder. The optical system is aligned within about a micrometer with the tip of flow sensor 110 to allow for the proper amount of light to be deflected. The optical system holder may include spaces and/or attachment mechanisms (e.g., latches, clasps, couplings, etc.) for each of prism mirror 122, ball lens 124, optical fiber 126, and focusing lens 128.

First inlet 102, first channel 104, first outlet 106, second inlet 114, second channel 118, and second outlet 120 may form an interconnected flow channel for the fluid. First inlet 102 and second outlet 120 may include a nozzle.

Although not shown in FIG. 1, fluidic device 100 may include a first conduit coupled to first inlet 102. Likewise, a second conduit may be coupled to second outlet 120. A third conduit may also be present. Fluidic device 100 may also include a valve positioned between the first conduit and the third conduit. The third conduit may be in fluid communication with an inlet of the valve. The first inlet of the first channel is in fluid communication with an outlet of the valve. A reservoir may be positioned between the second conduit and the valve.

First channel 104 and second channel 118 may have a length between about 1 mm and 20 mm. First channel 104 and second channel 118 may have a diameter between about 0.1 mm and about 3 mm. First channel 104 may be positioned in a first compartment and second channel 118 may be positioned in a second compartment. The first compartment and second compartment may be coupled and/or removably coupled to one another such that fluid sensor 110 is positioned between first outlet 106 and second inlet 114. The first compartment and second compartment may be transparent. First outlet 106 may have a longitudinal axis that is substantially (+/−5%) perpendicular to a longitudinal axis of fluid sensor 110. Layer 108 may include a biocompatible material, such as polydimethylsiloxane (PDMS), polypropylene, polyvinil alcohol, acetal plastics, parylene, poly (tetrafluroethylene), poly(methymethacrylate), and/or poly(ether-urethanes).

Fluid sensor 110 may include a sensor designed in the following manner: SU-8 negative photoresist polymer is first patterned on an aluminum substrate to fabricate sensors by the photolithography technique. A 1:1 mixture of SU-8 2005 and SU-8 thinner is used to form the 2 μm-thick cantilever. Then, SU-8 2005 is patterned on top of the first layer to fabricate the 15 μm-thick frame. The third step is to deposit a thin layer of titanium by thermal deposition. The sacrificial aluminum substrate is wet-etched by Ferric chloride. The sensor may also be fabricated using other methods.

In operation, once fluidic device 100 is deployed, fluid begins to flow through first inlet 102, into first channel 104, and through first outlet 106. The fluid flows through fluid sensor 110. When the fluid flows through fluid sensor 110, fluid sensor 110 may bend, changing the angle at which it deflects light. The fluid may then flow through second opening 114, into second channel 118, and through second outlet 120.

Further, to detect proper flow through fluidic device 100, medical personnel may focus a high-powered LED at a subject's skin. To align the LED with fluidic device 100, medical personnel may use an aligning tool. The aligning tool might only need to be accurate within a few millimeters to effectively pass light through the optical system and into flow sensor 110. The LED may pass through 2-3 mm of the subject's skin and hit prism mirror 122. Prism mirror 122 may redirect the light from the LED into ball lens 124, which is coupled to optical fiber 126. Ball lens 124 acts to funnel the light into the optical fiber to reduce any loss of light. The light travels through optical fiber 126, which acts as an aperture that delivers spatially-confined light to focusing lens 128. Focusing lens 128 receives and focuses the light towards flow sensor 110. If fluidic device 100 is working properly, the flow sensor 110 will redirect the light through opening 116 to the subject's skin. Medical personnel can then use an imaging device to sense the light coming through the subject's skin to determine that fluidic device 100 is functioning properly.

Data Analysis

Figure 2:
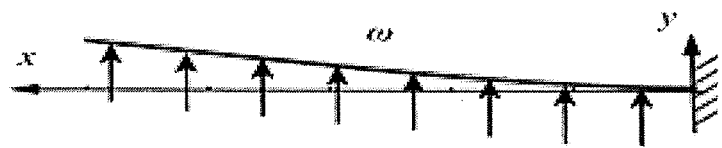
FIG. 2 shows a graph depicting sensor deflection due to uniformly distributed fluid pressure, according to an example embodiment.

FIG. 2 shows flow sensor 110 modelled as a cantilever, deflected by uniformly distributed fluid pressure. The deflection of the sensor is given as $$\delta y = \frac{\omega x^2 (x^2 - 4lx + 6l^2)}{24EI}$$

where I is the second momentum of area, E is young's modules, L is the length of the sensor, and ω is the distributed pressure from the water. The maximum deflection at y=1. can be rewritten as $$\delta y_{max} = \frac{\omega l^4}{8EI}$$

In this model, the deflection of the sensor is proportional to the equally distributed load from the water.

Figure 3:
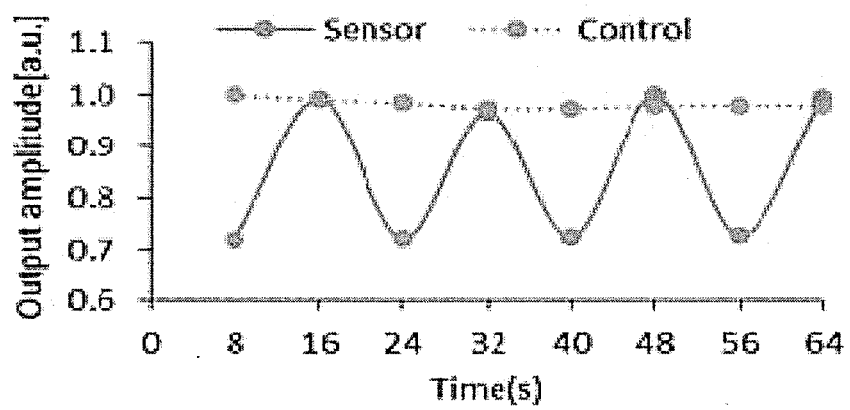
FIG. 3 shows a graph depicting sensor output with respect to time, according to an example embodiment.

FIG. 3 shows measured sensor output with respect to time when a pump is turned on and off every 8 seconds at a rate of 60 ml/hr. The dotted lines represent the varied light intensity measured at the tip of the cantilever. Control signal measured from the background is also shown in the figure. The light intensity reflected off of the sensor varied alternately when the pump was switched on and off, while the background intensity marginally changed. This shows the sensor deflection was caused by the fluid flow, rather than light noise or other circumstantial factors.

This manual pumping method may also be used to calibrate the flow sensor. For instance, CSF can be manually pumped at a known flow rate (e.g., 60 mL/hr) and correlated with the sensor output to record a baseline measurement. A subject's heart rate can also be monitored and correlated with the sensor output to establish the effect of CSF flow on the subject's heart rate.

Figure 4:
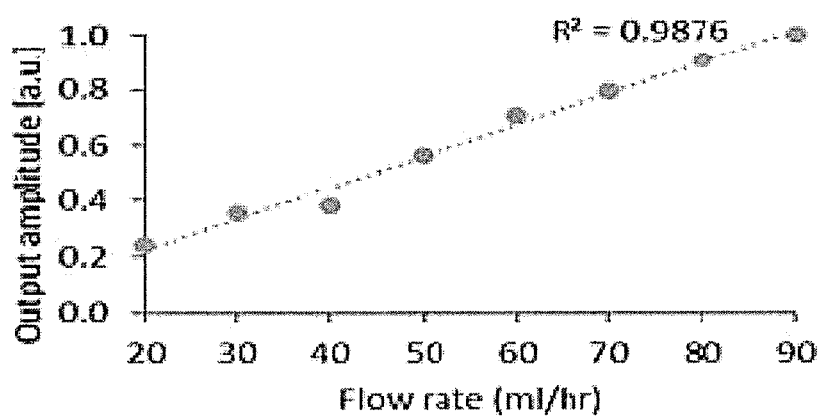
FIG. 4 shows a graph depicting the trend line of sensor output amplitude at different flow rates, according to an example embodiment.

FIG. 4 shows the trend line of sensor output amplitude at different flow rates. The amplitude of the sensor in each flow rate goes up as the flow rate increases. The bending angle of the sensor caused by fluid flow was measured to be proportional to the flow rate.

The fluidic device described herein may include microscale-standing cantilevers in an elastic material with piezoresistors on the hinges that detect deformation by measuring change in resistance. These microscale devices may be integrated into the fluidic device by adjusting the cantilever to a size of 200×1000 microns from polyimide, with a metal for biocompatibility and reflectance coating. The metals may include gold, platinum, iridium, iridium oxide, Titanium, titanium alloys, and CoCr alloys. The cantilever may have a thickness between about 20 nanometers and about 20 micrometers. Given that the cantilevers change their reflectivity based on bending from flow, medical personnel may detect the change in reflectivity via infrared (IR) light, which is known to easily penetrate skin and soft tissue, and that can be detected by CCD devices such as those used in cellphone cameras.

The fluidic device is designed to be compatible with conventional shunts (e.g., mechanical tubes or valves designed to redirect blood or other bodily fluids). The fluidic device may be implanted near the skin surface of the subject (5-20 mm depth), allowing for non-invasive sensing based on IR imaging of the flow sensor. The fluidic device may be manufactured to operate with or without battery power. The fluidic device may operate without the need of electrical power when only a deflection of the sensor is optically measured. Also, the fluidic device may be powered remotely by an external radio-frequency (RF) field or powered internally by an integrated battery.

The sensor may be the polymer-based cantilever located in the middle of the flow path. The cantilever is bent due to CSF flow, and the deflection is measured as the sensor response. Integration of different designs of cantilevers allows for simultaneous measurement of both CSF flow rates and pressures. It is also easily possible to integrate an electrical (active) strain sensor onto the flow sensor. Electrically activated flow sensors will be useful for future chronicle monitoring of CSF flow and pressure. One advantage of the described sensor is that it may be added to a conventional shunt, such as a ventriculoperitoneal (VP) shunt. The sensor can be added as an attachment to the VP shunt or integrated into a single device.

The sensor may also be a membrane valve that is configured to straighten when proper CSF flow is present. When the membrane valve straightens, the deflection can be measured as the sensor response.

In terms of detecting the signal, both optical (passive) and electrical (active) measurements of the different designs of cantilevers may be employed. In one particular example, IR imaging may be used. One possible configuration of IR imaging is using an IR LED (light emitting diode) array and a conventional CCD camera. With the wavelength range of 880-930 nm, sub-millimeter veins as deep as 3 mm under the skin surface have been successfully imaged. This methodology allows for use of a regular smart phone as a detection method. A better imaging depth (~4 mm) with lateral resolution of 12.5 μm has been demonstrated with laser based optical coherence tomography (OCT) with wavelengths ranging from 1200-1600 nm. The imaging depth in the flow sensor described herein is more effective than the above reported imaging methods, because (1) the gold mirror will create an optical contrast much higher than usually observed in human tissues, and (2) the main part of the light path is a flow sensor module filled with CSF, which is transparent for IR wavelengths.

Additional modes of transmission other than IR imaging are possible as well. The device may be arranged to communicate according to one or more other types of wireless communication (e.g., protocols) such as Bluetooth, microwaves, communication protocols described in IEEE 802.11 (including any IEEE 802.11 revisions), cellular technology (such as GSM, CDMA, UMTS, EV-DO, WiMAX, or LTE), Zigbee, dedicated short range communications (DSRC), and radio frequency identification (RFID) communications, among other possibilities.

Polymer Based Micro Flow Rate Sensing Cantilevers Fabrication Process

The complete fabrication process of polymer based micro flow rate sensing cantilevers is described as follows. SU-8 is a negative epoxy-based photoresist polymer which was patterned on the substrate by UV lithography technique. The first step was to pattern cantilever design on an aluminum substrate by a 1:1 mixture of SU-8 2005 and SU-8 thinner. Next, SU-8 2015 negative photoresist was patterned on top of the first layer to fabricate frame. The third step was to deposit a thin layer of titanium by thermal deposition. The sacrificial aluminum substrate was wet-etched by Ferric Chloride.

SU-8 Patterned on Aluminum Substrate to Form Cantilever and Frame

The first step was to pattern SU-8 on aluminum substrate with UV lithography. It is a process that uses ultraviolet (UV) light to transfer a desired pattern from a photomask onto the photosensitive material. A 1:1 mixture of SU-8 2005 and SU-8 thinner (MicroChem, USA) was used to form the 2 μm-thick cantilever. Next, the same fabrication process was followed to fabricate the 15 μm-thick frame by SU-8 2015 (MicroChem, USA).

Substrate Pretreat

Clean and dry substrates are efficient to obtain maximum process reliability before adding SU-8 photoresist. Aluminum sheets covered glass slides with dimensions 75 mm×35 mm were used as substrates. For best results, substrates were washed with Acetone during spinning coat and dried by itself as well.

Spin Coat

Uniform SU-8 photoresist covered the substrate with an expected thickness was accomplished by a spinning coater. The following programs were used to form a 2 μm-thick layer with a 1:1 mixture of SU-8 2005 and SU-8 thinner: (Step 1) Spin at 500 rpm for 10 seconds with acceleration of 100 rpm/second; (Step 2) Spin at 3000 rpm for 30 seconds with acceleration of 300 rpm/second. The same program was used to form a 15 μm-thick photoresist with SU-8 2015 for the second layer. Spin coating was followed by soft baking at 97° C. about 1 minute for the 2 μm-thick layer and 3 minutes for the 15 μm-thick layer. A level hotplate with thermal uniformity was used to conduct soft bake. The purpose of soft bake was to improve solvent evolution.

Exposure

The photomask was designed on L-Edit software. It defined geometric design of the desired cantilever and frame. The exposure process was conducted by a UV lithography machine. The pattern was transferred to SU-8 layer by illuminating Ultraviolet light onto the mask. The mask covered or exposed some area of underlying SU-8 layer. Therefore, the desired pattern was imaged to the SU-8 layer. After patterning the first cantilever layer, the second layer was aligned onto it using a mask aligner and alignment marks of the photomask. The exposure power of the UV lamp machine was 26.4 mW/cm$^2$. The exposure energy required for the 2 μm-thick SU-8 and the 15 μm-thick SU-8 were 80 mJ/cm$^2$, 140 mJ/cm$^2$. Considering the aluminum substrate was used, the relative dose was calculated to multiply the required exposure power by 1.5. So the exposure time for the 2 μm-thick cantilever was 4.5 seconds, and for the the 15 μm-thick cantilever was 8 seconds. After exposure, hard bake was carried out for 2 minutes for the cantilever layer and 4 minutes for the frame layer.

SU-8 Develop

Photoresists are materials that undergo photochemical reactions when exposed to light. There are two types of photoresists, negative and positive. Negative photoresist shows the unique feature, in which the exposed resist endures in developer, and the unexposed resist are soluble in developer. Positive photoresist shows opposite behavior. SU-8 photoresist used in this experiment is a negative photoresist. The SU-8 developer (MicroChem, USA) was used for development. It took 20 seconds and 1 minutes for the cantilever and the frame layer to be developed, respectively. Next, the developed sample was washed with IPA for 10 seconds, and then dried using the spinning coater.

Thin Titanium Film Deposition

After SU-8 patterning, the next step of the fabrication process was to deposit a thin titanium film on top of the SU-8 layers. Evaporation is a commonly used technique to deposit thin metal films. When the material is heated up in a vacuum, it evaporates into vapor particles, releases directly toward to the substrate, and forms a condense solid state. It is a type of physical vapor deposition (PVD), since there are no chemical reactions in the process. There are two types of evaporation machines, e-beam evaporation and resistive heat evaporation. And the second apparatus was used to conduct this experiment due to the lower melting points of titanium. It utilized the heat by inducing a current passing through a metal plate, in which the material was evaporated.

Wet Etching

After the SU-8 patterning and titanium deposition, the next step of the fabrication process was etching. Wet etching is a patterning process to transfer a two dimensional pattern onto a structural layer underneath the top masking layer. Ferric Chloride was an ideal etchant to conduct the etching process because both SU-8 and titanium were resistant, while sacrificial aluminum substrate etched by itself. Therefore, samples were removed from the substrate and collected for future research.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying Figures be interpreted as illustrative and not in a limiting sense. Further, it is intended to be understood that the following clauses (and any combination of the clauses) further describe aspects of the present description.

We claim:

1. A system, comprising:
   a fluidic device adapted to be positioned under a skin of
      a patient, the fluidic device comprising:

a first channel including a first inlet and a first outlet;

a second channel including a second inlet and a second outlet, wherein the second inlet of the second channel is in fluid communication with the first outlet of the first channel;

a sensor positioned between the first outlet and the second inlet, wherein the sensor comprises a membrane valve configured to deflect from a first position to a second position in response to a flow between the first channel and the second channel, and wherein the membrane valve includes one or more biocompatible reflective surfaces; and an optical system adapted to be positioned under the skin of the patient, wherein the optical system includes a focusing lens configured to focus light from a light source onto the membrane valve, wherein the one or more biocompatible reflective surfaces of the membrane valve are configured to deflect light from the membrane valve to an imaging device, wherein the imaging device is configured to measure a light intensity of light reflected off of the one or more biocompatible reflective surfaces of the membrane valve, and wherein the light intensity measured by the imaging device has a first value when the membrane valve is in the first position, wherein the light intensity measured by the imaging device has a second value when the membrane valve is in the second position in response to the flow between the first channel and the second channel, and wherein the second value is greater than or less than the first value.

2. The system of claim 1, wherein a longitudinal axis of the first outlet is substantially perpendicular to a longitudinal axis of the sensor, and wherein a flow at the first inlet of the first channel is substantially perpendicular to a flow across the sensor.

3. The system of claim 1, wherein the one or more biocompatible reflective surfaces include a metal selected from a list including gold, Platinum, iridium, iridium oxide, Titanium, titanium alloys, and CoCr alloys.

4. The system of claim 1, wherein the first inlet comprises a first nozzle.

5. The system of claim 1, wherein the second outlet comprises a second nozzle.

6. The system of claim 1, wherein the first channel is positioned in a first compartment, wherein the second channel is positioned in a second compartment, wherein the first compartment and the second compartment are coupled to one another such that the sensor is positioned between the first outlet of the first channel and the second inlet of the second channel.

7. The system of claim 6, wherein the first compartment and the second compartment are removably coupled to one another.

8. The system of claim 6, wherein a top surface of the second compartment includes an opening positioned above the sensor.

9. The system of claim 6, wherein the first compartment and the second compartment are transparent.

10. The system of claim 1, wherein the light source comprises an infrared light emitting diode, and wherein the imaging device comprises a charged coupled device (CCD) camera.

11. The system of claim 1, wherein the first channel has a length between about 1 mm and about 20 mm and/or wherein the second channel has a length between about 1 mm and about 20 mm.

12. The system of claim 1, wherein the first channel has a diameter between about 0.1 mm and about 3 mm, and/or wherein the second channel has a diameter between about 0.1 mm and about 3 mm.

13. The system of claim 1, wherein the optical system is aligned to the sensor by an optical system holder.

14. The system of claim 1, wherein the optical system comprises a prism mirror, an optical fiber, a ball lens positioned between the optical fiber and the prism mirror, and the focusing lens positioned between the optical fiber and the sensor, wherein the prism mirror is configured to deflect the light from the light source into the ball lens, wherein the ball lens is configured to focus the light into the optical fiber, wherein the optical fiber is configured to direct the light into the focusing lens, and wherein the focusing lens is configured to focus the light into the sensor.

15. The system of claim 14, wherein the prism mirror has a dimension of about 1 mm by 1 mm to 5 mm by 5 mm, and/or wherein the ball lens has a diameter of about 1 mm to 5 mm, and/or wherein the optical fiber has a diameter of about 0.5 mm to 3 mm, and/or wherein the focusing lens has a diameter of about 2 mm to 6 mm.

16. The system of claim 1, wherein the optical system comprises a prism mirror, an aperture, a hollow metal tube, and the focusing lens, wherein the prism mirror is configured to deflect the light from the light source into the aperture, wherein the aperture is configured to focus the light into the hollow metal tube, wherein the hollow metal tube is configured to direct the light into the focusing lens, and wherein the focusing lens is configured to focus the light into the sensor.

17. A method comprising:

positioning the system of claim 1 in a cerebral ventricle of a subject; and detecting, via a deflection in the membrane valve, a flow rate of a liquid between the first channel and the second channel.

18. A non-transitory computer readable medium having stored thereon instructions, that when executed by one or more processors, cause an additive manufacturing machine to create the system of claim 1.

19. A non-transitory computer readable medium having stored thereon instructions, that when executed by one or more processors, cause a system to perform operations comprising the steps of claim 17.

20. The system of claim 1, wherein the light source is adapted to be positioned above the skin of the patient, and wherein the imaging device is adapted to be positioned above the skin of the patient.

21. The system of claim 1, wherein the membrane valve is configured to straighten when the membrane valve is in the second position.

* * * * *